US008894490B2

(12) United States Patent
Brandt (10) Patent No.: US 8,894,490 B2
(45) Date of Patent: Nov. 25, 2014

(54) INTERACTIVE SPORTS GAMING DEVICE

(76) Inventor: Jordan Brandt, Red Bank, NJ (US)

( * ) Notice: Subject to any disclaimer, the term of this patent is extended or adjusted under 35 U.S.C. 154(b) by 180 days.

(21) Appl. No.: 12/851,594

(22) Filed: Aug. 6, 2010

(65) Prior Publication Data

US 2011/0034250 A1 Feb. 10, 2011

Related U.S. Application Data (60) Provisional application No. 61/232,048, filed on Aug. 7, 2009.

(51) Int. Cl.
*A63F 7/06* (2006.01)
*A63F 13/98* (2014.01)
*A61F 13/06* (2006.01)

(52) U.S. Cl.
CPC ......... *A63F 13/02* (2013.01); *A61F 2300/1043* (2013.01); *A63F 2300/1062* (2013.01); *A61F 13/06* (2013.01); *A61F 2300/407* (2013.01); *A63F 2300/105* (2013.01)
USPC ...................... 463/39; 463/3; 463/7; 473/288

(58) Field of Classification Search
USPC ...................... 463/3, 7, 36–39; 473/282, 288; D21/733
See application file for complete search history.

(56) References Cited

U.S. PATENT DOCUMENTS

| | | | |
|---|---|---|---|
| 3,779,559 A * | 12/1973 | Taylor | 473/285 |
| 2005/0017454 A1 | 1/2005 | Endo et al. | |
| 2007/0265075 A1 * | 11/2007 | Zalewski | 463/36 |
| 2008/0015017 A1 * | 1/2008 | Ashida et al. | 463/37 |
| 2008/0171596 A1 * | 7/2008 | Hsu | 463/39 |
| 2009/0118012 A1 * | 5/2009 | Sternberg | 463/37 |
| 2010/0203969 A1 * | 8/2010 | Takahashi et al. | 463/32 |
| 2010/0279771 A1 * | 11/2010 | Block et al. | 463/37 |
| 2011/0081968 A1 * | 4/2011 | Mar | 463/37 |
| 2011/0190056 A1 * | 8/2011 | Xu et al. | 463/36 |
| 2013/0196769 A1 * | 8/2013 | Shocklee | 463/37 |

OTHER PUBLICATIONS

Form PCT/ISA/220 "Notification of Transmittal of the International Search Report and Written Opinion of the International Searching Authory", Mailed Feb. 28, 2011 for PCT/US2010/044635, (2 Pgs).
Form PCT/ISA/201, "International Search Report", Mailed Feb. 28, 2011 for PCT/US2010/044635, (3 Pgs).
Form PCT/ISA/237, "Written Opinion of the International Searching Authority", Mailed Feb. 28, 2011 for PCT/US2010/044635, (4 pgs).

* cited by examiner

*Primary Examiner* — Damon Pierce
(74) *Attorney, Agent, or Firm* — Jon Fallon, Esq.; Michael P. Kochka, Esq.

(57) ABSTRACT

Embodiments of the present invention generally relate to an interactive sports gaming device and methods of manufacturing and utilizing same. More specifically, embodiments of the present invention relate to an interactive sports gaming device simulating the feel of an authentic sports accessory, capable of providing a cost-effective training device for actual sports play. In one embodiment of the present invention, an interactive sports gaming device comprises a housing for supporting a motion detection controller, the motion detection controller for wirelessly communicating with a video game system, and an authentic handle projecting from a first end of the housing, wherein the interactive sports gaming device simulates the feel of an authentic sports accessory.

8 Claims, 5 Drawing Sheets

INTERACTIVE SPORTS GAMING DEVICE

CROSS-REFERENCE TO RELATED APPLICATIONS

This application claims priority to pending U.S. Provisional Patent Application Ser. No. 61/232,048, filed Aug. 7, 2009, entitled "Interactive Sports Gaming Device," the disclosure of which is incorporated by reference herein in its entirety.

BACKGROUND

1. Field of the Invention

Embodiments of the present invention generally relate to an interactive sports gaming device and methods of manufacturing and utilizing same. More specifically, embodiments of the present invention relate to an interactive sports gaming device simulating the feel of an authentic sports accessory, capable of providing a cost-effective training device for actual sports play.

2. Description of the Related Art

People are often exposed to virtual gaming devices at a young age. These gaming devices are particularly appealing to children for the charm and convenience to enter a virtual world where, though there are gaming rules to follow, a player may essentially do what they please without suffering the social consequences of engaging in the same tasks in reality. For many people, particularly teenagers and young adults, virtual gaming devices become a reason to hold social gatherings, but also provide an introverted means of entertainment.

Common virtual gaming systems include: Atari, Nintendo, Sega Genesis, PlayStation, Xbox, Nintendo Wii and hundreds of others. Video gaming systems may also take the form of a personal computer or a general purpose computing device. Gaming controllers for these systems are often wireless, allowing the user mobility and freedom to play the gaming system from any position in a room. Games for these gaming systems are becoming increasingly realistic with three dimensional view points and motion detection controllers. However, a problem with these new and improved gaming systems and controllers is the lack of authenticity, for example, when playing a virtual sports game. For example, when playing a golf or tennis game on Nintendo Wii, the game can be easily dominated by hitting the virtual ball extremely hard and fast with a simple twist of a user's wrist. Of course, in a real golf or tennis match, such events could never occur.

In addition to mere child's play, technology is being utilized to provide sports simulation devices, whereby athletes are able to practice their athletic skills in a virtual environment. For example, in the golf industry, virtual indoor golf ranges provide a large screen showing a golfer's view of a golf course, and monitors a golfer's swing with a real golf club to determine where a virtual golf ball should travel when it is virtually hit. While such technology is quite fascinating, acquiring such devices can cost between $20,000 to almost $40,000 or more. Thus, for an average amateur golfer or the average golf fan, such devices are unacquirable.

Thus, there is a need in the industry for an interactive sports gaming device simulating the feel of an authentic sports accessory, capable of providing a cost-effective training device for actual sports play.

SUMMARY

Embodiments of the present invention generally relate to an interactive sports gaming device and methods of manufacturing and utilizing same. More specifically, embodiments of the present invention relate to an interactive sports gaming device simulating the feel of an authentic sports accessory, capable of providing a cost-effective training device for actual sports play. In one embodiment of the present invention, an interactive sports gaming device comprises a housing for supporting a motion detection controller, the motion detection controller for wirelessly communicating with a video game system, and an authentic handle projecting from a first end of the housing, wherein the interactive sports gaming device simulates the feel of an authentic sports accessory.

In another embodiment of the present invention, an interactive golf gaming device comprises a housing for supporting a motion detection controller, the motion detection controller for wirelessly communicating with a video game system, and an authentic golf shaft projecting from a first end of the housing, wherein the interactive sports gaming device simulates the feel of an authentic golf club.

In yet another embodiment of the present invention, an interactive sports gaming device comprises a housing for supporting a motion detection controller against a sensor portal of the housing, the motion detection controller, having a sensor, for wirelessly communicating with a video game system, and an authentic handle projecting from a first end of the housing, the authentic handle comprising a portion of one of an authentic golf club, baseball bat, hockey stick, tennis racquet, lacrosse stick, badminton racquet, cricket mallet, fencing sword, jai alai xistera, paddle ball paddle, squash racquet, or a polo mallet, wherein the interactive sports gaming simulates the feel of at least one of an authentic sports accessory.

BRIEF DESCRIPTION OF THE DRAWINGS

So the manner in which the above recited features of the present invention can be understood in detail, a more particular description of embodiments of the present invention, briefly summarized above, may be had by reference to embodiments, which are illustrated in the appended drawings. It is to be noted, however, the appended drawings illustrate only typical embodiments of embodiments encompassed within the scope of the present invention, and, therefore, are not to be considered limiting, for the present invention may admit to other equally effective embodiments, wherein.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning may). Similarly, the words "include", "including", and "includes" mean including but not limited to. To facilitate understanding, like reference numerals have been used, where possible, to designate like elements common to the figures.

DETAILED DESCRIPTION

In the following detailed description, numerous specific details are set forth in order to provide a thorough understanding of exemplary embodiments or other examples described herein. However, it will be understood that these examples may be practiced without the specific details. In other instances, well-known methods, procedures, and components have not been described in detail, so as to not obscure the following description. Furthermore, the examples disclosed herein are for exemplary purposes only and other examples may be employed in lieu of, or in combination with, the examples disclosed.

Embodiments of the present invention generally relate to an interactive sports gaming device and methods of manufacturing and utilizing same. More specifically, embodiments of the present invention relate to an interactive sports gaming device simulating the feel of an authentic sports accessory, capable of providing a cost-effective training device for actual sports play.

For purposes of embodiments of the present invention, the terms "authentic sports accessory," including variations and derivatives thereof, should be defined as a piece of sporting equipment, generally known to amateur and professional athletes in the sport, and generally recognized by those in the sport as being an acceptable piece of equipment for the sport. For example, in one embodiment, where an interactive sports gaming device is intended to be utilized in conjunction with a golf video game, an "authentic sports accessory" may include a golf club, or portion thereof, having regulation weight, length and/or overall size range of parameters, dictated by regulatory agencies governing the game. Throughout the present disclosure, the term "authentic," may be provided next to a specific sports accessory. Where such use of the term is provided, this definition of "authentic sports accessory" in general should be applied to such specific use of the term, to the extent the specific sports accessory may be authentic in the industry of the specific game.

For purposes of embodiments of the present invention, the phrase "simulating the feel of an authentic sports accessory," including variations or derivatives thereof, should be understood by those of ordinary skill in the art as providing a tactile and sensory feel substantially similar to an authentic piece of sports equipment. For example, in one embodiment, where an interactive sports gaming device is intended to be utilized in conjunction with a golf video game, those of ordinary skill in the art should appreciate without visually looking at the interactive sports gaming device, the weight, physical grip, overall feeling, and non-visual sensory perception, when properly holding the interactive sports gaming device feels substantially similar to an authentic sports accessory.

Figure 1:
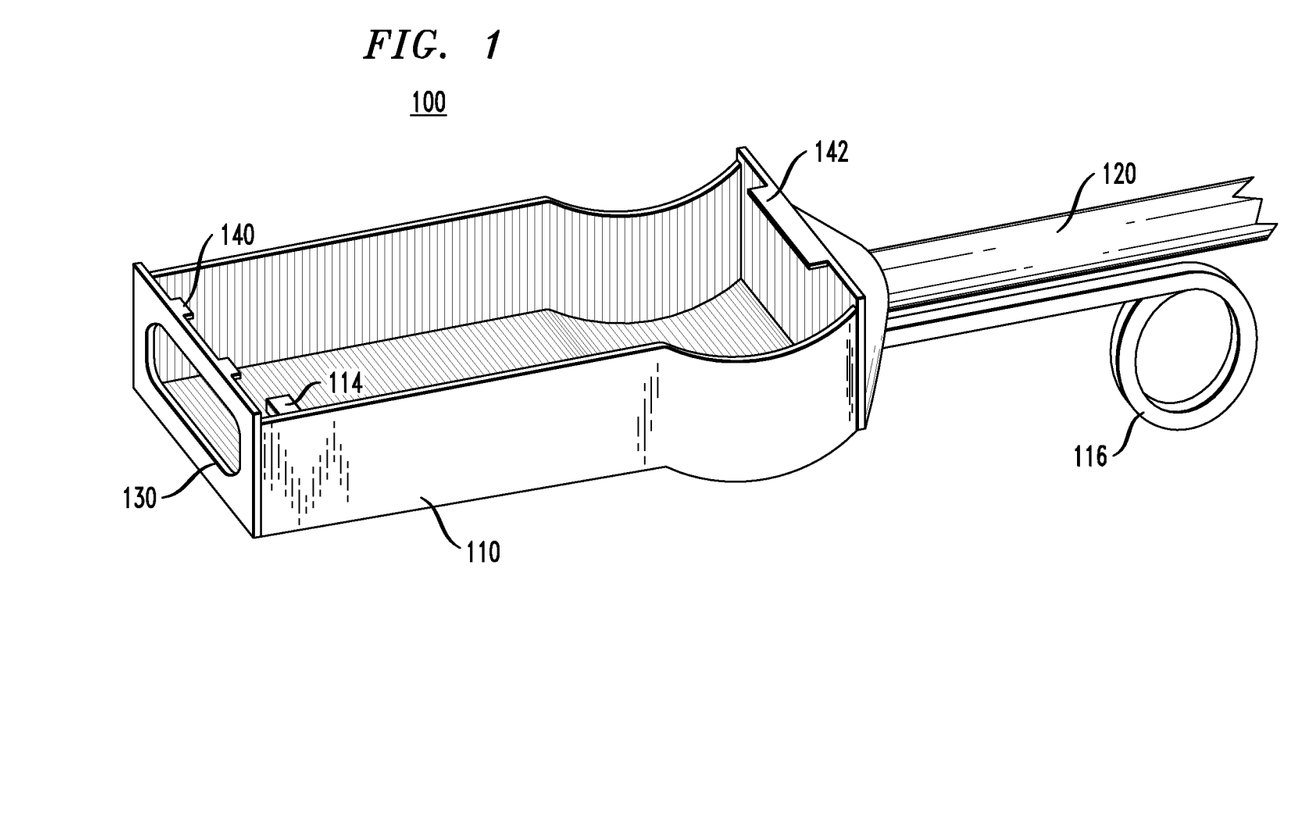
FIG. 1 depicts a perspective view of an interactive sports gaming device in accordance with one embodiment of the present invention.

FIG. 1 depicts an interactive sports gaming device in accordance with one embodiment of the present invention. Generally, an interactive sports gaming device 100 comprises a housing 110 for a motion detection controller (not shown), molded of plastic, metal, wood, or the like, and an authentic handle 120. The housing 110 may be shaped in a rectangle, square, oval, circle, or the like. In many embodiments, the housing 110 substantially comprises an interior volume open on a top surface. Optionally, the housing 110 may comprises a sensor portal 130, which may allow a sensor of a motion detection controller to be exposed therethrough.

Generally, the authentic handle 120 may include the authentic look and feel of any stick used in a sport which may give the player a more realistic feel when playing a virtual sports game. These sports may include, but are not limited to, golf, baseball, hockey, tennis, lacrosse, badminton, cricket, fencing or the like. As such, the authentic handle 120 may substantially comprise all or a portion of a golf club, a baseball bat, a hockey stick, a tennis racquet, a lacrosse stick, a badminton racquet, a cricket paddle, a fencing sword, a jai alai xistera, a paddle ball paddle, a squash racquet, a polo mallet or the like. The authentic handle 120 has the look and feel of an authentic sports accessory as to simulate a more realistic feeling of playing a virtual sports game.

In one embodiment, the authentic handle 120 may comprise an authentic grip, for example, a golf grip. Golf grips may include soft grips or hard grips, and are available in half corded or full corded. Golf grip cords may be available in classic, GX, tour wrap, or the like. Types of golf grips include, but are not limited to, rubber (a blend of liquid rubber and granulated cork), polymer (Ethylene Propylene Diene Monomer, for example), leather (cowhide or calfskin), corded (a cotton-thread blend), or the like. The weight of a golf grip may range from less than 20 grams to almost 70 grams. The majority of grips range from 40 to 55 grams.

Another embodiment of the present invention may utilize an authentic handle 120 resembling the look and feel of an authentic baseball bat. The authentic handle 120 for a baseball bat may comprise of a material including, but not limited to, white ash, maple, aluminum (which may be lined with titanium, or graphite, or other material), hickory, bamboo, or the like. The authentic handle 120 for a baseball bat may be wrapped with tape (not shown) or the like according to a player's individual preference.

In another embodiment of the present invention the interactive sports gaming device may comprise an authentic handle 120 resembling the look and feel of an authentic hockey stick (not shown). The authentic handle 120 for a hockey stick may comprise of a material or combination of materials including, but not limited to, wood, aluminum, fiberglass, carbon fiber (e.g., graphite), Kevlar, or the like. Similar to that of other sports sticks, the holding portion of a hockey stick may be wrapped or taped (e.g., friction tape, cloth tape, etc.) according to a player's individual preference.

In yet another embodiment of the present invention, the interactive sports gaming device may comprise an authentic handle 120 resembling the look and feel of an authentic lacrosse stick (not shown). The authentic handle 120 for a lacrosse stick may comprise of a material or combination of materials including, but not limited to, aluminum, graphite, titanium, Kevlar, alloys of aluminum, magnesium, scandium, zinc, wood or the like. Similar to that of other holding portions of authentic handles 120, the authentic handle 120 may be wrapped or taped according to a player's individual preference.

In a further embodiment of the present invention, the interactive sports gaming device may comprise an authentic handle 120 resembling the look and feel of an authentic tennis racket (not shown). The authentic handle 120 for a tennis racket may comprise of a material or combination of materials including, but not limited to, fiberglass, Kevlar, titanium, texalium, liquid metal, wood or the like. Similar to that of other holding portions or grips of authentic handles 120, the authentic handle 120 may be wrapped or taped according to a player's individual preference.

The authentic handle 120 may be removable and detachable to the motion detection controller 110. If the authentic handle 120 is not essential to a specific interactive game, it may be removed and stored away for later use. In certain embodiments, an attachment means may be provided whereby which the authentic handle 120 may be attached (e.g., via a screw, snap-lock, friction fit, or the like) to the back of the motion detection controller 110. This also allows for an array of authentic handles 120 to be conveniently and easily interchangeable for different virtual games.

In some embodiments, an engagement means 116 may provided to control an engagement tab 114. Often, when a motion detection controller is provided in the housing, the engagement tab 114 is positioned adjacent thereto, against an action button of the motion detection controller, as described in more detail hereinbelow. Accordingly, when a user desires to engage or activate the action button, the engagement means may be utilized by the user.

Figure 2:
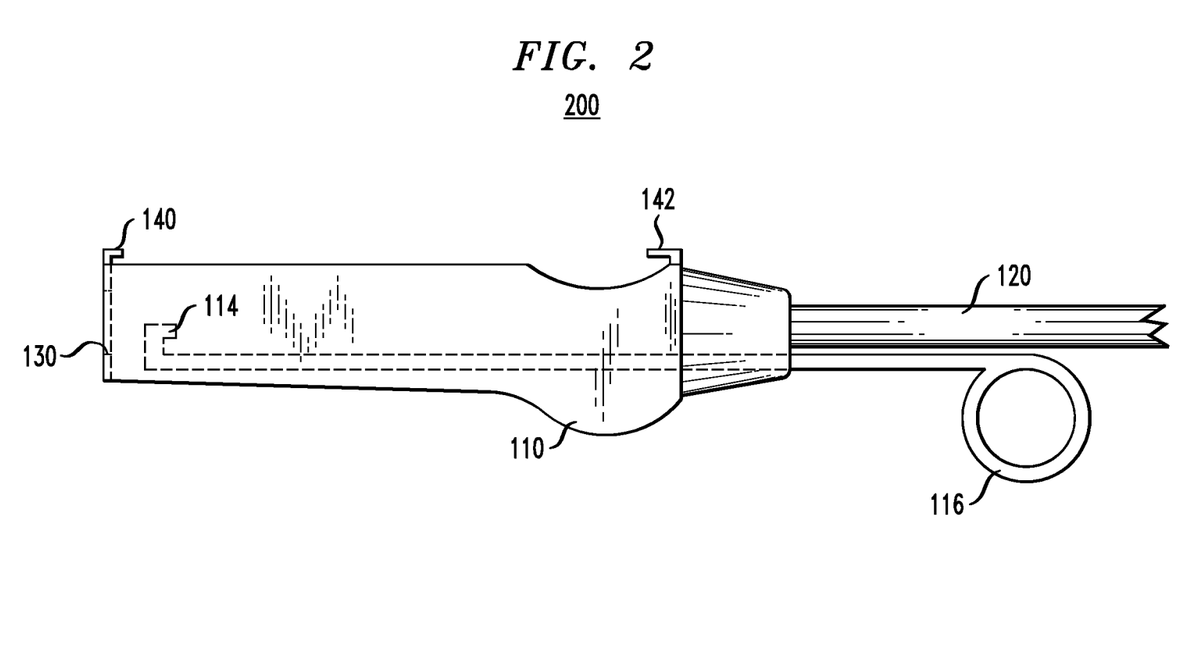
FIG. 2 depicts a side view of an interactive sports gaming device in accordance with one embodiment of the present invention.

As shown in FIG. 2, which depicts a side view of an interactive sports gaming device 200 in accordance with one embodiment of the present invention, an engagement means 116 comprises a loop and shaft combination, extending parallel to the authentic handle 120. The engagement means 116 may extend through a portion of the housing 110, and terminates with an engagement tab 114. In many embodiments, the engagement means 116 is spring biased within the housing, such that when a user pulls the loop of the engagement means 116 away from the housing and subsequently releases it, the engagement means 116 returns to its normal state.

In many embodiments, the size and positioning of the engagement means 116 is dependent upon the nature of the authentic handle 120. In one embodiment of the present invention, the engagement means 116 may extend out a length suitable to reach and maneuver while a user is holding the authentic handle 120 with the same hand. A player may grip the authentic handle 120 with one or two hands, while holding the engagement means 116 with a finger of the one or two hands. Accordingly, depending upon the nature of the authentic handle, the engagement means 116 may comprise any structure suitable to enable a user holding the interactive sports gaming device 100 to engage the engagement means 116 and thus, the action button, without substantially altering the normal holding position of the interactive sports gaming device 100.

In accordance with embodiments of the present invention, a securing tab 140 may be provided on the housing 110 to retain a motion detection controller when utilized therein. Such securing tab 140 may comprise any projection off the housing suitable to prevent a motion detection controller from inadvertently falling out of the housing when in use. Similarly, in certain embodiments, a release tab 142 may also be provided. In such embodiments, the release tab 142 may be movably biased within the housing 110 to allow a motion detection controller to easily be inserted and removed from the housing 110.

Figure 3:
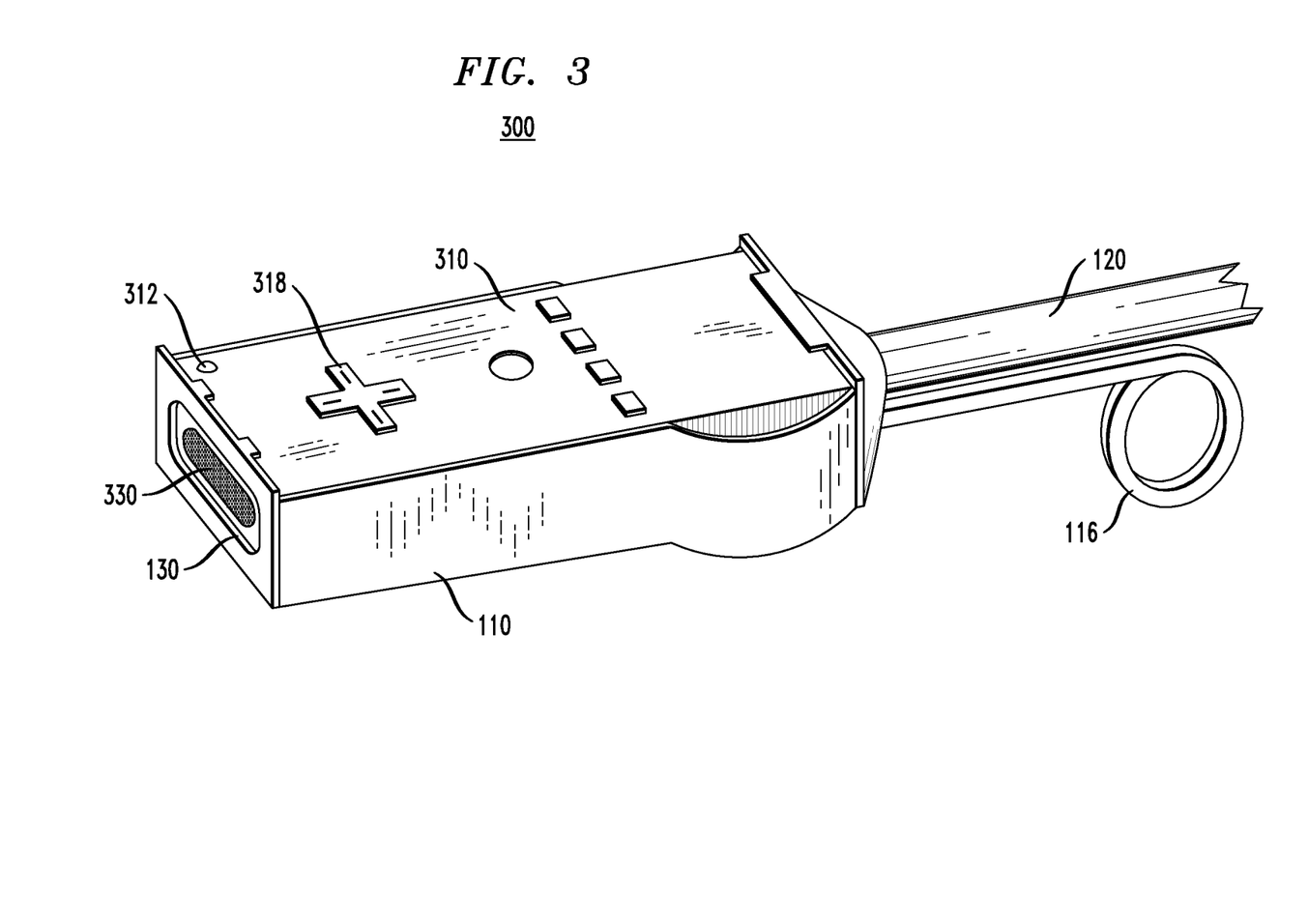
FIG. 3 depicts an interactive sports gaming device having a motion detection controller in accordance with one embodiment of the present invention.

FIG. 3 depicts an interactive sports gaming device having a motion detection controller in accordance with one embodiment of the present invention. As shown in the Figure, an interactive sports gaming device 300 may comprise a housing 110, an authentic handle 120 and a motion detection controller 310. The motion detection controller, which is optional, may be used for any gaming unit which allows for a motion detection controller, such as Wii, PlayStation, Xbox, any future gaming device compatible with a motion detection controller, or the like.

The motion detection controller 310 may comprise a sensor 330, for example, on the front of the motion sensor controller 310 or embedded otherwise therein, to be pointed in the general direction of a gaming unit or video game system or signal receiving devices. It should be appreciated however, the sensor may be embedded in any position on or within the motion detection controller. In some embodiments, the sensor 330 may comprise any active or passive sensor capable of receiving or sending signals regarding the nature of the motion of an interactive sports gaming device when utilized in accordance with embodiments of the present invention. While the motion detection controller 310 is in use, the sensor 330 may be pointed in the general direction of the gaming unit in order to sync the motion detection controller 310 to the gaming unit. The sensor 330 is able to transmit signals from the motion of the motion detection controller 330 and send it to the gaming unit to mimic the movement of the player onto the virtual object or character on the game.

In some embodiments, the motion detection controller 310 may further comprise a power button 312. The power button 312 may be used to power the motion detection controller 310 on and off to save power when not in use. The motion detection controller 310 may power off when not used for a period of time, but may also be manually powered off.

Figure 4:
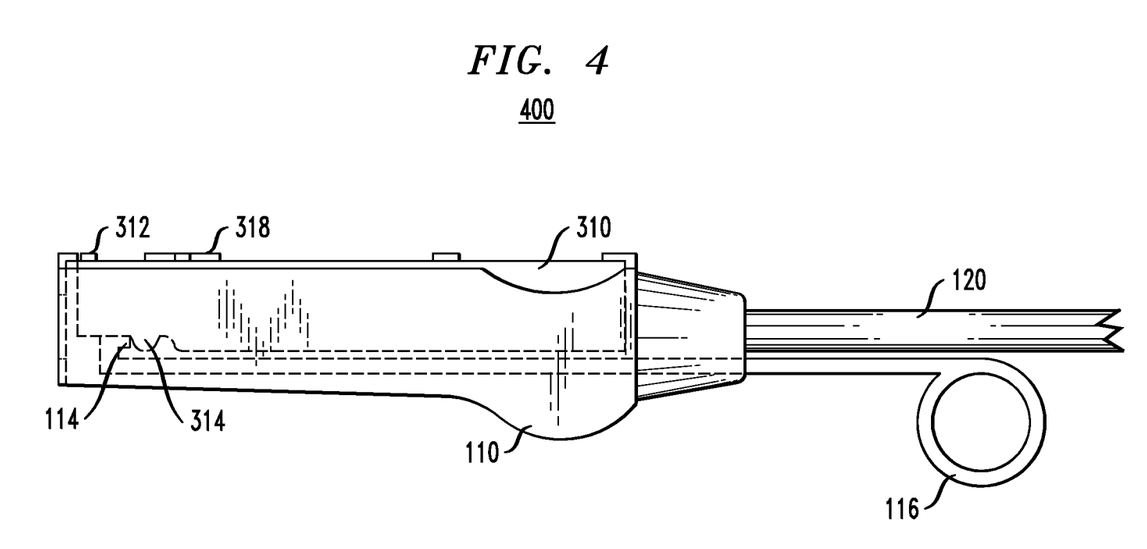
FIG. 4 depicts a side view of an interactive sports gaming device having a motion detection controller in accordance with one embodiment of the present invention.

FIG. 4 depicts a side view of an interactive sports gaming device having a motion detection controller in accordance with one embodiment of the present invention. The motion detection controller 310 may further comprise an action button 314. In certain embodiments, the positioning of the action button 314 on the bottom of the motion detection controller 310 allows for operation quickly and reliably when needed.

In many embodiments, the action button 314 allows for a player character or object to perform an arbitrary action such as punching, throwing, capturing, obtaining, riding, jumping, or the like. For example, in an action game, the action button 314 makes it possible to designate jumping, punching, firing a weapon, hitting, stroking, passing, running, etc. Alternatively, in a role-playing game or a simulation of the like, the action button 314 makes it possible to designate the obtainment of an item, the selection of a weapon, a ball, a stick, a puck, a shuttlecock, a command prompt, or the like.

As described above, in one embodiment, the action button 314 is positioned to be in physical or electrical communication with an engagement tab 114 of an engagement means 116. It should be appreciated, however, the engagement means 116 may comprise any physical, electrical, magnetic, or optical means of activating the action button 314. Although described herein as a button, the action button 314 may comprise any means of instructing the motion detection controller to take an action.

In some embodiments, a directional switch 318 is provided on the motion detection controller 310. The directional switch 318 is a combined switch of multi-direction push switches and center switch, and includes forward or up, backward or down, right, and left, and in several embodiments, any direction therebetween. By operating or pushing any of the multi-directional push switches or center switch, it is possible to designate a movement direction of a character or object capable of being operated by a player or to designate a movement in the direction of a cursor. The directional switch 318 may also be used as a joystick, or the like.

In various embodiments of the present invention, a player's hand movements may define the movement of a virtual object or character. Movements may include, but are not limited to, toggling or cradling of the motion detection controller 110 to denote a virtual object or character running in the game.

Furthermore, a plurality of buttons (not shown) may be positioned on the motion detection controller 310. The plurality of buttons may be used to make adjustments to view point positions and view point directions in displaying a three-dimensional image. For example, in a lacrosse game or other sports game which requires an open space, one of the plurality of buttons may be used to make adjustments to a position and a field angle of a virtual camera, as well as displaying one or more game menus. Essentially, the motion detection controller 310 may be adaptable to any gaming device with corresponding buttons and directional switches, as necessary.

Optionally, embodiments of the present invention may further comprise a wristband (not shown). The wristband is connected to the motion detection controller and is adjustable in length to fit the wrist of the player holding the interactive sports gaming device. The wristband may be for the protection of the player and for the protection of the objects, persons, and general surroundings of the player, as to ensure that the interactive sports gaming device does not spin or fly out of control if accidentally dropped or released while in use.

In one embodiment of the present invention, the housing 110 may fully encase and contain the motion detection controller 310, as if the housing itself were the motion detection controller. For example, in one embodiment, the housing 110 may comprise a fully encased volume and the motion detection controller 310 may comprise a plurality of hardware stored therein.

In such an embodiment, the housing may comprise a battery compartment (not shown) having a lid which is detachable to allow for concealing the battery while in use. The lid may be detached and removed when the battery may be replaced. Batteries used to power the interactive sports gaming device may include, but are not limited to, zinc-carbon, zinc chloride, alkaline (e.g., AA, AAA), silver-oxide, lithium ion, or the like. In lieu of a battery, in various embodiments of the present invention, the motion detection controller 110 may be electrically powered from any known AC or DC power source or supply.

In some embodiments of the present invention, the housing 110 may comprise a weight compartment (not shown) to further assist in the simulation of using an authentic sports accessory. The weight of an authentic sports accessory may be more accurately replicated through weight regulation within the housing 110. Although referred to as a weight compartment, such weight regulation may be obtained through the modification of any amount of mass within the housing, the motion detection controller, or external thereto. In one embodiment, a plurality of weights may be contained within the weight compartment. In another embodiment, lead tape or similar commercially available mass adding device may be utilized within the housing 110 to achieve such weight regulation.

In one embodiment, a plurality of weights may be placed in individual compartments within a weight compartment to ensure less movement of the plurality of weights while the interactive sports gaming device is in movement. The weight compartment may be concealed with a lid, similar to that of the battery lid discussed above. The lid may be detached and removed when the plurality of weights may be replaced or removed.

Figure 5A:
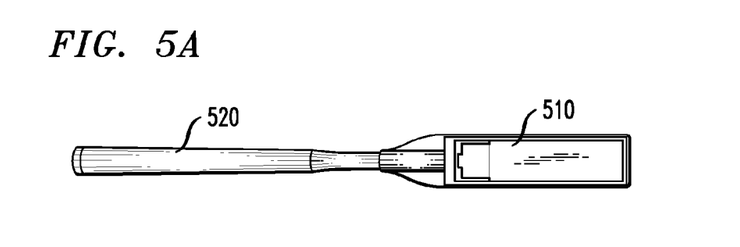
FIG. 5a depicts an interactive golf gaming device in accordance with one embodiment of the present invention.

FIGS. 5a-5d depict exemplary embodiments of interactive sports gaming devices, in accordance with embodiments of the present invention. FIG. 5a depicts an interactive golf gaming device in accordance with one embodiment of the present invention. As shown in the Figure, the interactive golf gaming device comprises a housing 510 connecting on first end to an authentic golf shaft 520, having a golf grip thereon.

Figure 5B:
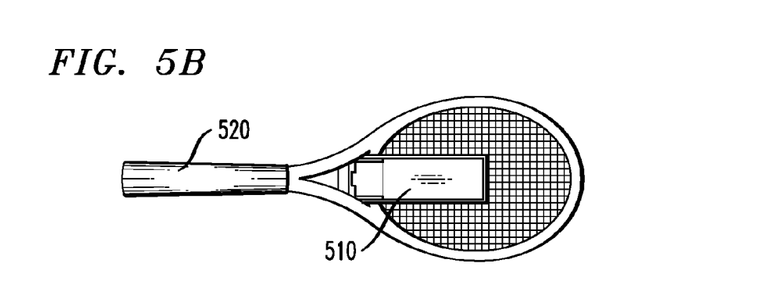
FIG. 5b depicts an interactive tennis gaming device in accordance with one embodiment of the present invention.

FIG. 5b depicts an interactive tennis gaming device in accordance with one embodiment of the present invention. As shown in the Figure, the interactive tennis gaming device comprises a housing 510, surrounded by a simulated tennis racquet head, connected to a tennis handle 520, having a grip thereon.

Figure 5C:
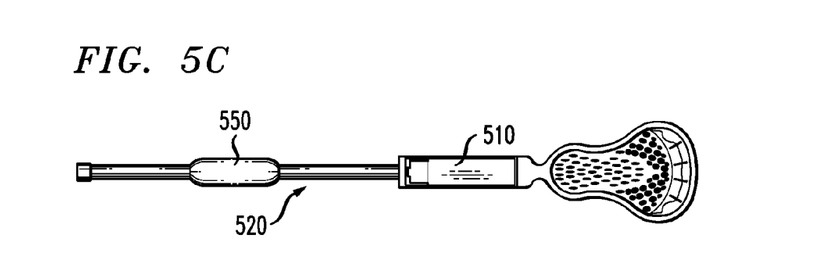
FIG. 5c depicts an interactive lacrosse gaming device in accordance with one embodiment of the present invention.

FIG. 5c depicts an interactive lacrosse gaming device in accordance with one embodiment of the present invention. As shown in the Figure, the interactive lacrosse gaming device comprises a housing 510, an optional lacrosse head affixed to a second end of the housing, and a lacrosse shaft 520. In some embodiments, for example, with devices designed for lacrosse, hockey, or any other sports requiring a stick or accessory and an open field or ice rink, a secondary controller 550 may be provided at some point along the shaft 520. Such secondary controller may be utilized to monitor a secondary motion, such as running down a field or skating across ice or other function required by the game. Although the secondary controller 550 may be substantially similar to the motion detection controller 310 described herein, in some embodiments, the secondary controller 550 provides a tactile directional device or other game functions thereon. An exemplary commercially available secondary controller is sold by Nintendo, Inc., branded as the "Nunchuk."

Figure 5D:
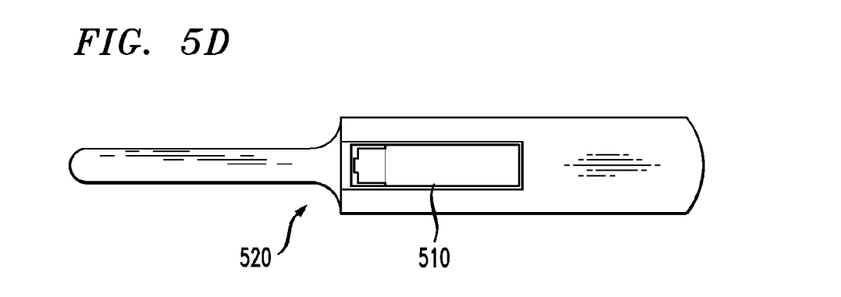
FIG. 5d depicts an interactive cricket gaming device in accordance with one embodiment of the present invention.

FIG. 5d depicts an interactive cricket gaming device in accordance with one embodiment of the present invention. As shown in the Figure, the interactive cricket gaming device comprises a housing 510, surrounded by a simulated paddle, connected to a cricket handle 520.

While the foregoing is directed to embodiments of the present invention, other and further embodiments of the invention may be devised without departing from the basic scope thereof. Alternative embodiments of the present invention generally incorporate the structures and methods described in the embodiments above, with minor additions and/or modifications. The features of the disclosed embodiments may be considered independently or in combination with any other feature of any other embodiment contained herein, to create yet further embodiments of the present invention.

What is claimed is:

1. An interactive golf gaming device comprising:
 a housing for supporting a motion detection controller, the motion detection controller for wirelessly communicating with a video game system;
 an authentic golf handle projecting from a first end of the housing, the authentic golf handle comprising a shaft attached to the first end of the housing and a grip disposed over a portion of the shaft, the shaft comprising an exposed portion disposed between the grip and the first end of the housing; the shaft and the grip extending in a straight line away from the first end of the housing, the first end of the housing positioned opposite a front end of the motion detection controller; and
 an engagement means extending through a portion of the housing terminating with an engagement tab, the engagement tab positioned against an action button of the motion detection controller, the engagement means comprising a loop attached to a shaft, the shaft extending parallel to the authentic handle;
 wherein the authentic golf handle comprises an authentic weight and size of an authentic golf handle.

2. The interactive golf gaming device of claim 1, wherein the shaft comprises a metal or metal alloy shaft; and
wherein the housing comprises plastic.

3. The interactive golf gaming device of claim 1, wherein the grip comprises a rubber, a blend of liquid rubber and granulated cork, a polymer, leather, a cotton-thread cord, or combinations thereof.

4. The interactive golf gaming device of claim 1, further comprising a protective wrist band for removably securing the interactive golf gaming device to a user's wrist.

5. An interactive sports gaming device comprising:
a housing for supporting a motion detection controller against a sensor portal of the housing, the motion detection controller, having a sensor on a front end of the motion detection controller, for wirelessly communicating with a video game system; and
an authentic handle projecting from a first end of the housing, the authentic handle comprising a shaft attached to the first end of the housing and a grip disposed over a portion of the shaft, the shaft comprising an exposed portion disposed between the grip and the first end of the housing; the shaft and the grip extending in a straight line away from the first end of the housing, the first end of the housing positioned opposite the sensor portal and the front end of the motion detection controller, the sensor portal formed in a front wall of the housing, the front wall maintaining the motion detection controller against the sensor portal within the housing, the authentic handle comprising a portion of one of an authentic golf club, baseball bat, hockey stick, tennis racquet, lacrosse stick, badminton racquet, cricket mallet, fencing sword, jai alai xistera, paddle ball paddle, squash racquet, or a polo mallet; and
an engagement means extending through a portion of the housing terminating with an engagement tab, the engagement tab positioned against an action button of the motion detection controller, the engagement means comprising a loop attached to a shaft, the shaft extending parallel to the authentic handle;
wherein the authentic handle comprises an authentic weight and size of one of an authentic golf club, baseball bat, hockey stick, tennis racquet, lacrosse stick, badminton racquet, cricket mallet, fencing sword, jai alai xistera, paddle ball paddle, squash racquet, or a polo mallet.

6. The interactive sports gaming device of claim 5, wherein the authentic handle comprises a portion of a baseball bat made from one of white ash, maple, aluminum, titanium, graphite, hickory, bamboo or combinations thereof.

7. The interactive sports gaming device of claim 5, wherein the authentic handle comprises a portion of a hockey stick made from one of wood, aluminum, fiberglass, carbon fiber, Kevlar or combinations thereof.

8. The interactive sports gaming device of claim 5, wherein the authentic handle comprises a portion of a tennis racquet made from one of fiberglass, Kevlar, titanium, texalium, liquid metal, wood or combinations thereof.

* * * * *